(12) United States Patent
Siljamäki et al.

(10) Patent No.: US 9,814,908 B2
(45) Date of Patent: Nov. 14, 2017

(54) APPARATUS AND METHOD PERTAINING TO MOVEMENT COMPENSATION DURING RADIATION TREATMENT

(75) Inventors: Sami Siljamäki, Helsinki (FI); Janne Nord, Espoo (FI); Michelle Marie Svatos, Oakland, CA (US); Corey E. Zankowski, San Jose, CA (US); Stanley Mansfield, Sunnyvale, CA (US)

(73) Assignees: Varian Medical Systems International AG, Cham (CH); Varian Medical Systems, Inc., Palo Alto, CA (US)

( * ) Notice: Subject to any disclaimer, the term of this patent is extended or adjusted under 35 U.S.C. 154(b) by 45 days.

(21) Appl. No.: 13/286,754

(22) Filed: Nov. 1, 2011

(65) Prior Publication Data

US 2013/0109904 A1 May 2, 2013

(51) Int. Cl.
*A61N 5/10* (2006.01)

(52) U.S. Cl.
CPC ......... *A61N 5/1045* (2013.01); *A61N 5/1037* (2013.01); *A61N 5/1067* (2013.01); *A61N 5/107* (2013.01); *A61N 2005/105* (2013.01)

(58) Field of Classification Search
CPC .. A61N 5/1045; A61N 5/1049; A61N 5/1064; A61N 5/1065; A61N 5/1067; A61N 5/1069; A61N 5/107; A61N 2005/105; A61N 2005/1051; A61N 2005/1059
USPC .......................................................... 600/1
See application file for complete search history.

(56) References Cited

U.S. PATENT DOCUMENTS

| | | | |
|---|---|---|---|
| 6,144,875 A | 11/2000 | Schweikard et al. | |
| 7,822,176 B2 * | 10/2010 | Yi et al. | 378/65 |
| 2007/0164230 A1 | 7/2007 | Rigney et al. | |
| 2010/0150309 A1 | 6/2010 | Nord et al. | |
| 2011/0015521 A1 * | 1/2011 | Faul | 600/426 |
| 2011/0200170 A1 | 8/2011 | Nord et al. | |

FOREIGN PATENT DOCUMENTS

EP 2085118 A1 8/2009

OTHER PUBLICATIONS

Han, In Ho; Authorized officer; PCT Search Report and Written Opinion from related application No. PCT/US2012/061930 dated Feb. 26, 2013; 11 pages.
Shirato et al., "Physical Aspects of a Real-Time Tumor-Tracking System for Gated Radiotherapy," Int. J. Radiation Oncology Biol. Phys., vol. 48, No. 4; pp. 1187-1195; 2000.
(Continued)

*Primary Examiner* — John Lacyk
*Assistant Examiner* — Thaddeus Cox
(74) *Attorney, Agent, or Firm* — Fitch, Even, Tabin & Flannery LLP

(57) ABSTRACT

A control circuit controls real-time administration of a radiation-treatment plan that administers a therapeutic radiation dose to a patient. This includes compensating for a first movement as regards the application setting using a first treatment-administration modality and responding to detection of a second movement by using a second treatment-administration modality that is different from the first treatment-administration modality.

4 Claims, 2 Drawing Sheets

(56) References Cited

OTHER PUBLICATIONS

Seppenwoolde et al., "Precise and Real-Time Measurement of 3D Tumor Motion in Lung Due to Breathing and Heartbeat, Measured During Radiotherapy," Int. J. Radiation Oncology Biol. Phys., vol. 53, No. 4; pp. 882-834; 2002.
Tewatia et al., "Clinical Implementation of Target Tracking by Breathing Synchronized Delivery," Med. Phys. vol. 33, No. 11; Nov. 2006; pp. 4330-4336.
D'Souza et al., "An Analysis of the Treatment Couch and Control System Dynamics for Respiration-Induced Motion Compensation," Med. Phys. vol. 33, No. 12; Dec. 2006; pp. 4701-4709.
Sawant et al., "Management of Three-Dimensional Intrafraction Motion Through Real-Time DMLC Tracking," Med. Phys. vol. 35, No. 5; May 2008; pp. 2050-2061.
George et al., "On the Accuracy of a Moving Average Algorithm for Target Tracking During Radiation Therapy Treatment Delivery," Med. Phys. vol. 35, No. 6; Jun. 2008; pp. 2356-2365.
Extended European Search Report from related European Patent Application No. 12844830.5 dated May 22, 2015; 5 pages.

\* cited by examiner

APPARATUS AND METHOD PERTAINING TO MOVEMENT COMPENSATION DURING RADIATION TREATMENT

TECHNICAL FIELD

This invention relates generally to radiation treatment and more particularly to accommodating movement during radiation treatment.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted structures and adjacent tissues, organs, or the like that are desired or even critical to continued survival of the patient. As a result, radiation is ordinarily applied in a carefully administered manner to at least attempt to restrict the radiation to a given target volume.

That said, however, there are numerous challenges to administering radiation doses as intended. The radiation-treatment application setting, for example, typically comprises a physically-dynamic setting. In particular, a given radiation-treatment session will typically span at least many minutes and various scene components can move during that time.

Some of these movements can be predictable, at least to an extent. The patient, for example, can be expected to breathe periodically during the treatment course and this can cause various organs and tissues to move with respiration. Many other types of movement can occur, however. For example, an expected periodic movement (such as a respiration-based movement) can vary unexpected with respect to its periodicity (and hence experience a drift in movement phase) and/or its amplitude. Yet other types of movement can be random (as when, for example, the patient sneezes) and have no discernable relationship to a periodic or otherwise expected movement.

Unfortunately, existing approaches to attempt to compensate for movement during radiation treatment are not fully satisfactory for all application settings.

BRIEF DESCRIPTION OF THE DRAWINGS

The above needs are at least partially met through provision of the apparatus and method pertaining to movement compensation during radiation treatment described in the following detailed description, particularly when studied in conjunction with the drawings, wherein.

Figure 1:
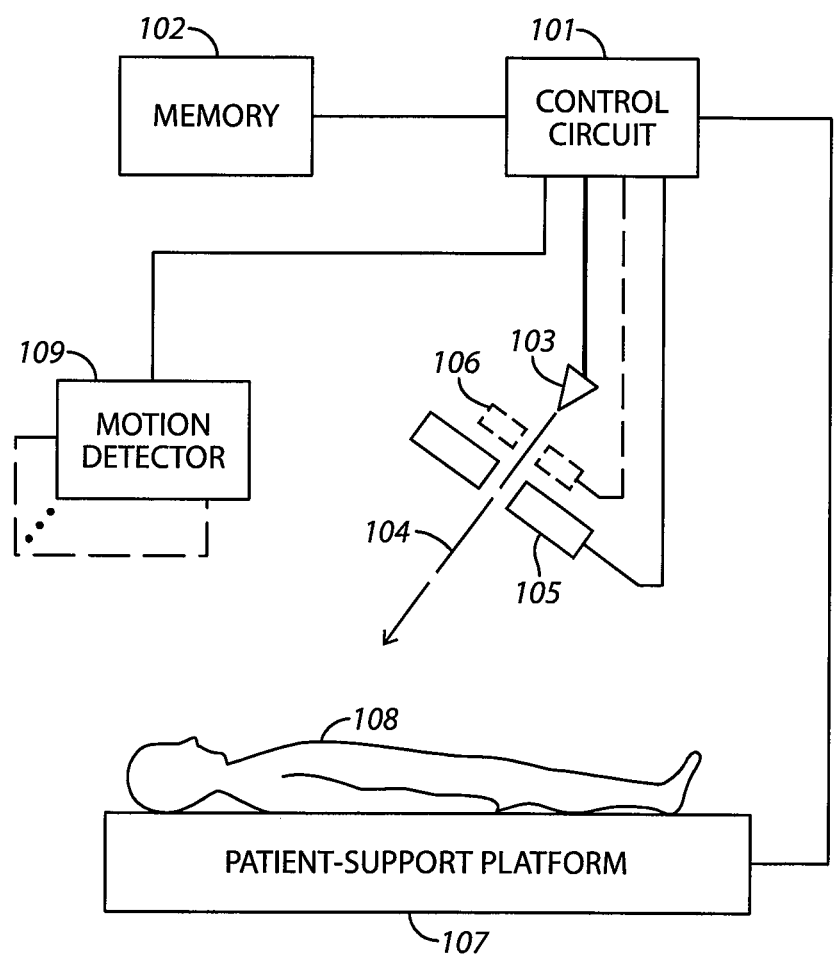
FIG. 1 comprises a block diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit is configured to control real-time administration of a radiation-treatment plan that administers a therapeutic radiation dose to a patient. This includes compensating for a first movement as regards the application setting using a first treatment-administration modality and responding to detection of a second movement by using a second treatment-administration modality that is different from the first treatment-administration modality.

By one approach, the aforementioned first movement comprises, at least to an extent, expected movement that the radiation-treatment plan takes into account. The second movement, then, can comprise, at least in part, unexpected movement (for example, unexpected movement as pertains to the patient). By another approach, in lieu of the foregoing or in combination therewith, the first movement can comprise, for example, a periodic movement while the second movement comprises a drift (for example, in movement phase) with respect to the periodic movement.

Generally speaking, these teachings will accommodate a wide variety of movement types. The first movement can comprise, for example, any of a random movement, a movement comprising a drift from a given position, a movement comprising a drift in movement phase, or a movement comprising a periodic movement. By one approach, whichever of these movement types/components (or combination of movement types/components), the second movement can comprise a movement type/component that is different than the first movement type/component.

The referred-to treatment-administration modalities can vary with the application setting. Examples include, but are not limited to, adjusting a multi-leaf collimator, adjusting a patient-support platform, gating application of a radiation beam, and so forth.

So configured, the efficacy of the radiation treatment need not rely upon only a single treatment-application modality when compensating for movement. This, in turn, permits these teachings to effect a useful result in a wide variety of application settings and circumstances. For example, different kinds (and/or degrees) of movement may be better accommodated by differing treatment-application modalities. By one approach these teachings permit a mix of treatment-application modalities to be utilized to better leverage their individual capabilities in these regards.

These teachings also facilitate improving the efficacy of radiation treatment by recognizing, and accommodating, that different kinds of movement can and will occur in a radiation-treatment application setting. By recognizing and accommodating these differing kinds of movement these teachings can leverage the usability and efficacy of a variety of existing treatment platforms.

The various approaches described herein are highly scalable and can be used with a variety of movement types as well as treatment-administration modalities. In many cases these teachings can also be implemented in a given application setting in an economically feasible manner.

These and other benefits may become clearer upon making a thorough review and study of the following detailed description. Referring now to the drawings, and in particular to FIG. 1, an illustrative implementation setting for administering a therapeutic radiation dose will be described.

In this illustrative example a control circuit 101 operably couples to a memory 102. Such a control circuit 101 can comprise a fixed-purpose hard-wired platform or can comprise a partially or wholly programmable platform. All of these architectural options are well known and understood in the art and require no further description here. For the sake of this example and without intending any limitations in these regards the remainder of this description will presume the control circuit 101 to be at least partially programmable.

The memory 102 serves to store, for example, computer instructions that, when executed by the control circuit 101, cause the control circuit 101 to carry out one or more of the steps, actions, or functions described herein. This memory 101 can also serve to store, as desired, a radiation-treatment plan. Such plans are known in the art and generally comprise a plurality of settings for one or more components that control or otherwise influence the provision of radiation to the patient. The present teachings will accommodate a wide variety of control plans and plan-formulation methodologies.

The control circuit 101 operably couples to one or more radiation treatment-administration components as desired. In this example, this includes coupling to the radiation source 103 (which provides a therapeutic radiation beam 104) and a multi-leaf collimator 105. The control circuit 101 can also operably couple to any number of additional beam-shaping components 106 as may be available for use and as desired.

Collimators are often used to restrict and form a radiation-therapy beam. Some collimators have a fixed aperture. Other collimators have an aperture that can be adjusted in one or more dimension Adjustable apertures permit, to at least some degree, customization of the radiation-therapy beam's cross section to thereby attempt to better match the requirements of a given target volume. The aforementioned multi-leaf collimator 105 is an example of such a component. Multi-leaf collimators are comprised of a plurality of individual parts (known as "leaves") that are formed of a high atomic-numbered material (such as tungsten) that can move independently in and out of the path of the radiation-therapy beam 104 in order to selectively block (and hence shape) the beam.

In this illustrative example the control circuit 101 also operably couples to a patient-support platform 107 that serves to support part or all of the patient 108 during the administration of the radiation. This patient-support platform 107 can comprise, for example, a couch. Patient-support platforms can be movable. This movement may be restricted to a single axis (such as up-and-down or left-and-right) or may be multi-dimensional. In some cases the patient-support platform 107 may be selectively movable up-and-down, side-to-side, rotationally, and/or with respect to pitch or inclination. The present teachings will also accommodate using a patient-support platform 107 having separably movable components (such as arm rests and/or leg rests that are separately movable with respect to a torso support surface).

So configured, the control circuit 101 can selectively and separately control these various radiation-administration components during a given radiation treatment. This means, for example, that the control circuit 101 can increase, decrease, or otherwise gate the energy of the radiation beam 104, open, close, or otherwise alter the aperture of one or more collimators, and/or move all or portions of the patient's body as desired during the course of treatment.

These various components, employed thusly, comprise different treatment-administration modalities. To illustrate by way of a trivial example, the control circuit 101 can employ any of these modalities to stop exposing the patient to the radiation beam 104. In particular, the control circuit 101 can gate the radiation source 103 off, or close the multi-leaf collimator's 105 aperture, or move the patient-support platform 107 sufficiently to move the patient 108 away from the path of the radiation beam 104 to achieve such a result.

That said, these various treatment-administration modalities are not all necessarily equally suited to effect a particular result in these regards. These modalities can differ, for example, with respect to the speed at which a given result can be achieved, the dimensional range over which a given result can be achieved, and/or a particular direction or orientation of correction that can be accommodated. Referring again to the simple example provided above, halting exposing the patient 108 to the radiation beam 104 can likely be more quickly accomplished by gating the radiation source 103 than by moving the patient 108 via the patient-support platform 107. The present teachings permit the control circuit 101 to utilize various treatment-administration modalities to effectively achieve specific results as pertain to movement that occurs while administering a therapeutic radiation treatment.

To facilitate such an approach, the control circuit 101 also operably couples to one or more motion detectors 109. Various motion detectors are known in the art. These include optical systems that utilize, for example, one or more lasers to detect absolute and/or relative movement of the patient's body. Other approaches can include a variety of imaging approaches and methodologies. As the present teachings are not particularly sensitive to any particular choices in these regards, further elaboration will not be provided here in such regards.

Figure 2:
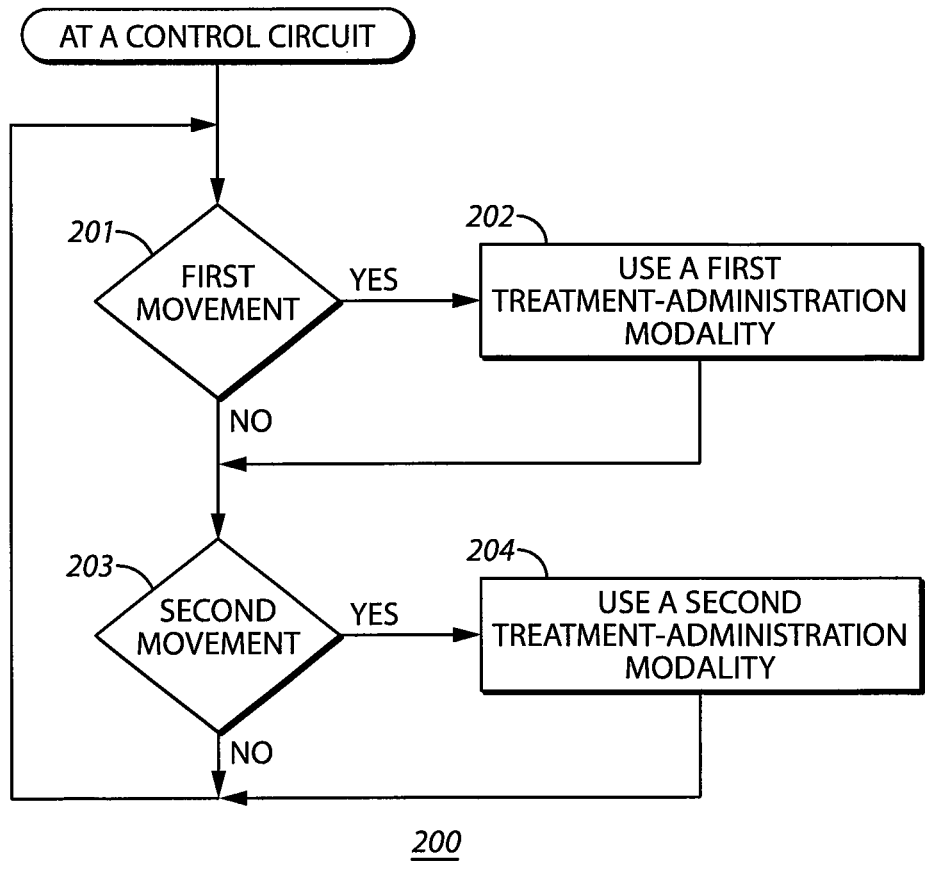
FIG. 2 comprises a flow diagram as configured in accordance with various embodiments of the invention.

FIG. 2 presents one illustrative approach in these regards. Pursuant to this process 200, at step 201, the control circuit (using, for example, the aforementioned motion detector(s) 109) detects (typically though not necessarily in real time (i.e., essentially immediately) or near real time (i.e., within, say, a few tens of milliseconds)) a first movement. This first movement can comprise, for example, a movement that pertains to a patient who is receiving a therapeutic radiation treatment. These teachings will accommodate a great variety of movements in these regards.

As one example in these regards, this first movement can comprise a movement that the pre-determined radiation-treatment plan takes into account. By way of illustration, certain movements of the patient may be anticipated and hence planned for. This might comprise a biological movement (such as patient breathing) or a non-biological movement (as when the patient-support surface moves (and hence moves the patient) as per the radiation-treatment plan).

As another example in these regards, this first movement can comprise a categorical type of movement. By way of illustration, this can include any of a random movement (for example, when the patient sneezes or moves a limb), a movement comprising a drift from a given position (for example, when the patient breathes cyclically as expected, but draws a deeper than expected breath and hence the full amplitude of the intake drifts from an expected amplitude), a movement comprising a drift in movement phase (for example, when the patient breathes cyclically as expected but where the breathing cycle shifts earlier or later in time than expected), or a movement comprising a periodic movement (for example, a regular, cyclical breathing pattern).

Pursuant to step 202 the control circuit 101 compensates for the detected first movement using a first treatment-administration modality. This might comprise, for example, adjusting the aperture and/or position/orientation of a multi-leaf collimator to accommodate that first movement. As one illustrative example in this regard, this can comprise compensating for the patient's regular, periodic breathing by adjusting a multi-leaf collimator. By one approach this use of the multi-leaf collimator to account for the patient's anticipated breathing cycle can comprise a part of the radiation-treatment plan. By another approach this can occur pursuant to a more real-time dosing methodology.

At step 203 this process 200 also has the control circuit 101 monitor for a second movement. By one approach (for example, when the first movement and the first treatment-administration modality pertain to planned-for movements), this second movement can comprise an unexpected movement as pertains to the patient.

By another approach, in lieu of the foregoing or in combination therewith, this second movement can comprise a type of movement that is categorically different from the first movement. As an illustrative example, the first movement can comprise a periodic movement and the second movement can comprise any of a movement comprising a drift (with respect to amplitude and/or phase) as pertains to that periodic movement or a random movement that is unrelated to the periodic movement.

The control circuit 101 responds to detection of this second movement, at step 204, by using a second treatment-administration modality that is different from the first treatment-administration modality. When the first movement comprises a planned-for expected movement and the first treatment-administration modality comprises adjustment of a multi-leaf collimator, and the second movement comprises an unexpected movement, the second treatment-administration modality might comprise, for example, movement of a patient-support platform 107.

Numerous other examples are readily accommodated by these teachings. For example, the first movement might comprise a periodic movement or a drift as pertains to that periodic movement while the second movement might comprise a random movement. In this case, and again for the purpose of illustration and without intending any limitations in these regards, the first treatment-administration modality might comprise use of both a multi-leaf collimator and a patient-support platform while the second treatment-administration modality might comprise gating application of the radiation beam 104 (for example, momentarily shutting off the radiation source 103 until the second movement abates).

Figure 3:
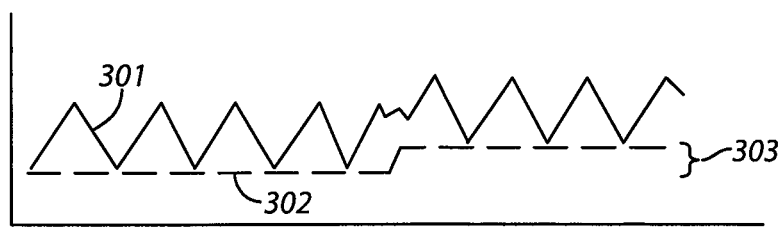
FIG. 3 comprises a graph as configured in accordance with various embodiments of the invention.

FIG. 3 illustrates a simple example in these regards. Here, the general waveform 301 represents movement associated with the patient's breathing over time. As shown, that breathing pattern is regular over time and therefore the positional effect of that breathing upon an acted-upon tissue is predictably cyclical as well. In this example, however, the baseline 302 of that positional movement shifts slightly (as represented by reference numeral 303) due to, for example, some small shift in position by the patient. In such a case, the control circuit 101 may accommodate the cyclical breathing-induced movement 301 by use of a first treatment-application modality such as a multi-leaf collimator and the baseline drift 303 in amplitude movement by use of a second treatment-application modality such as the patient-support platform 107.

As noted, these approaches will accommodate a real-time application setting (with or without a corresponding pre-calculated treatment plan). In such a case these teachings will accommodate a rapid analysis of incoming streaming position information (using, for example, a three-dimensional trend analysis approach over rolling time windows) in order to separate the principle movement components in order to facilitate employing different compensation strategies for differing movement components.

By one approach, each movement trend may be estimated to have a three-dimensional dose-time vector. In such a case the control circuit may be configured, for example, to determine how to assign effective compensation amongst all (or at least some) of the degrees of freedom that the application setting may afford (such as gantry positioning, collimator rotation or translation, multi-leaf collimator leaf positions, table translation or rotation, dose rate, and so forth). This need not be limited to a simple assignment of one kind of motion to a particular corresponding compensation axis. Instead, and as desired, these teachings will accommodate, for example, determining a given part (such as a principle component) of existing net motion that can be handled via one compensation axis and determining at least one remaining portion of that same net motion that can be compensated using a different compensation axis.

Furthermore, movement compensation can be calculated and parsed for a given patient based not only on the limits of the application setting itself (such as the relevant limits to machine movement and/or speed of movement) but also in terms of what is optimal for patient safety and comfort (which may differ from one patient to the next for a variety of reasons).

These teachings are highly flexible and scalable in practice and will accommodate a wide variety of radiation-treatment methodologies, types of movement components, and radiation treatment-administration modalities. By taking these various components into account a treatment planner or administrator can suitably leverage the advantages of a particular treatment-administration modality to match and efficiently compensate for a particular corresponding kind of movement or movement component.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. As one illustrative example in these regards, these teachings can serve to facilitate detecting in real-time the position of a target (such as a radiation-treatment target) and then using a decision-making circuit that utilizes the real-time position signal to identify which detected motions are accounted for in the treatment plan and which are not and, for motions that are not accounted for in the plan, categorizing the motion components to identify an appropriate type of compensation that can be responsively taken (for example, by adapting a machine motion axis or changing the amount of radiation being emitted as a beam).

We claim:

1. An apparatus to facilitate administering a therapeutic radiation dose, the apparatus having a plurality of different treatment-administration modalities that are not all necessarily equally suited to effect a particular result, the apparatus comprising:

a plurality of radiation treatment-administration components including a radiation source that provides a therapeutic radiation beam, at least one radiation beam collimator, and a selectively movable patient-support platform;

a memory having a radiation-treatment plan stored therein specifying use of the plurality of radiation treatment-administration components to administer the therapeutic radiation dose, the radiation-treatment plan including radiation-administration instructions to compensate for predictably-cyclical patient movement wherein the predictably-cyclical patient movement has a corresponding baseline of positional movement;

a control circuit operably coupled to the memory and to the plurality of radiation treatment-administration components and being configured to, while controlling in real time administration of the radiation-treatment plan using the plurality of radiation treatment-administration components, use a rules-based approach to:

compensate for the predictably-cyclical patient movement using a first treatment-administration modality to implement the radiation-administration instructions; and respond to detection of a persistent change to the baseline of positional movement of the predictably-cyclical patient movement by selecting from amongst the plurality of different treatment-administration modalities to identify a second treatment-administration modality that is different from the first treatment-administration modality and that is optimal for at least one of patient safety and comfort to use to compensate for the persistent change to the baseline of positional movement of the predictably-cyclical patient movement.

2. The apparatus of claim 1 wherein the second treatment-administration modality comprises movement of the patient-support platform.

3. A method for use with an apparatus having a plurality of different treatment-administration modalities that are not all necessarily equally suited to effect a particular result to facilitate administering a therapeutic radiation dose, the method comprising:

at a control circuit that is operably coupled to a plurality of radiation treatment-administration components including a radiation source that provides a therapeutic radiation beam, at least one radiation beam collimator, and a selectively movable patient-support platform and that is configured to use a rules-based approach to control real-time administration of a radiation-treatment plan using the plurality of radiation treatment-administration components that administers a therapeutic radiation dose to a patient, the radiation-treatment plan including radiation-administration instructions to compensate for predictably-cyclical patient movement wherein the predictably-cyclical patient movement has a corresponding baseline of positional movement:

compensating for the predictably-cyclical patient movement using a first treatment-administration modality to implement the radiation-administration instructions; and responding to detection of a persistent change to the baseline of positional movement of the predictably-cyclical patient movement by selecting from amongst the plurality of different treatment-administration modalities to identify a second treatment-administration modality that is different from the first treatment-administration modality and that is optimal for at least one of patient safety and comfort to use to compensate for the persistent change to the baseline of positional movement of the predictably-cyclical patient movement.

4. The method of claim 3 wherein the second treatment-administration modality comprises movement of the patient-support platform.

\* \* \* \* \*